United States Patent
Asakura et al.

(10) Patent No.: US 9,464,936 B2
(45) Date of Patent: Oct. 11, 2016

(54) PLASMA PROCESSING APPARATUS AND ANALYZING APPARATUS

(71) Applicant: HITACHI HIGH-TECHNOLOGIES CORPORATION, Tokyo (JP)

(72) Inventors: Ryoji Asakura, Tokyo (JP); Akira Kagoshima, Tokyo (JP); Daisuke Shiraishi, Tokyo (JP); Kenji Tamaki, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 485 days.

(21) Appl. No.: 14/023,831

(22) Filed: Sep. 11, 2013

(65) Prior Publication Data

US 2014/0262029 A1    Sep. 18, 2014

(30) Foreign Application Priority Data

Mar. 15, 2013   (JP) .................................. 2013-052634

(51) Int. Cl.
*H01J 37/32* (2006.01)
*G01J 3/443* (2006.01)
*G01N 21/68* (2006.01)

(52) U.S. Cl.
CPC ............... *G01J 3/443* (2013.01); *G01N 21/68* (2013.01); *H01J 37/32972* (2013.01); *H01J 2237/334* (2013.01)

(58) Field of Classification Search
CPC .. H01L 22/34; H01L 21/67069; G01J 3/443; H01J 37/32972; H01J 2237/334; G01N 21/68
See application file for complete search history.

(56) References Cited

U.S. PATENT DOCUMENTS 5,546,322 A    8/1996  Gifford et al.
2011/0315661 A1    12/2011  Morisawa et al.

FOREIGN PATENT DOCUMENTS

| JP | 8-62141 A | 3/1996 |
| JP | 3179997 B2 | 4/2001 |
| JP | 2005-077325 A | 3/2005 |
| JP | 4086190 B2 | 5/2008 |
| KR | 2011-0084302 A | 7/2011 |
| WO | 2010106712 A1 | 9/2010 |

OTHER PUBLICATIONS

Korean Office Action received in Korean Application No. 2013-110924 dated Aug. 13, 2014.

*Primary Examiner* — Jeffrie R Lund
*Assistant Examiner* — Yuechuan Yu
(74) *Attorney, Agent, or Firm* — Mattingly & Malur, PC

(57) ABSTRACT

An etching apparatus calculates an emission intensity in the vicinity of each of a plurality of wavelengths, at which a specified element should emit light, from information indicating light emission measured by an optical emission spectroscope during etching processing and, if it is determined that the calculated emission intensity information and emission intensity information stored in a storage unit are similar, extracts a wavelength, corresponding to the calculated emission intensity, with the wavelength associated with the element.

9 Claims, 14 Drawing Sheets

FIG. 5

| | WAFER ID | 1 | 2 | ... | 100 |
|---|---|---|---|---|---|
| WAVELENGTH EMISSION-INTENSITY | WAVELENGTH | | | | |
| | 200.0 | 179.8 | 180.1 | ... | 181.0 |
| | 200.2 | 180.0 | 181.2 | ... | 181.4 |
| | ... | ... | ... | ... | ... |
| | 800.0 | 117.7 | 119.8 | ... | 120.1 |
| PROCESSING RESULT 1 | | FAIR | EXCELLENT | ... | EXCELLENT |
| PROCESSING RESULT 2 | | 0.75 | 0.80 | ... | 0.78 |

| ELEMENT | WAVELENGTH | EMISSION INTENSITY | RANK |
|---|---|---|---|
| Al | 308.2 | 180 | |
| Al | 309.3 | 240 | |
| Al | 394.4 | 270 | 2 |
| Al | 396 | 280 | 1 |
| AlCl | 261.4 | 180 | 1 |
| AlCl | 264.8 | 130 | |
| AlCl | 268.3 | 140 | 2 |
| ... | ... | ... | ... |

| THRESHOLD 1 | THRESHOLD 2 |
|---|---|
| 0.7 | 0.8 |

| ELEMENT | WAVELENGTH | SPECIFIED ELEMENT | EMISSION INTENSITY | RANK |
|---|---|---|---|---|
| Al | 308.2 | ○ | 385 | 1 |
| Al | 309.3 | ○ | — | — |
| Al | 394.4 | ○ | 330 | 2 |
| Al | 396 | ○ | 320 | 3 |
| AlCl | 261.4 | ○ | 250 | 1 |
| AlCl | 264.8 | ○ | 210 | 3 |
| AlCl | 268.3 | ○ | 225 | 2 |
| AlH | 424.1 | | | |
| ⋮ | ⋮ | ⋮ | ⋮ | ⋮ |

FIG. 9

| ELEMENT 27b | WAVELENGTH 27c | RECOMMENDED ELEMENT 27d | RECOMMENDED WAVELENGTH 27e |
|---|---|---|---|
| Al | 308.2 | | |
| Al | 309.3 | | |
| Al | 394.4 | | |
| Al | 396 | | |
| AlCl | 261.4 | ○ | ○ |
| AlCl | 264.8 | ○ | |
| AlCl | 268.3 | ○ | |
| AlH | 424.1 | | |
| ... | ... | ... | ... |

27a

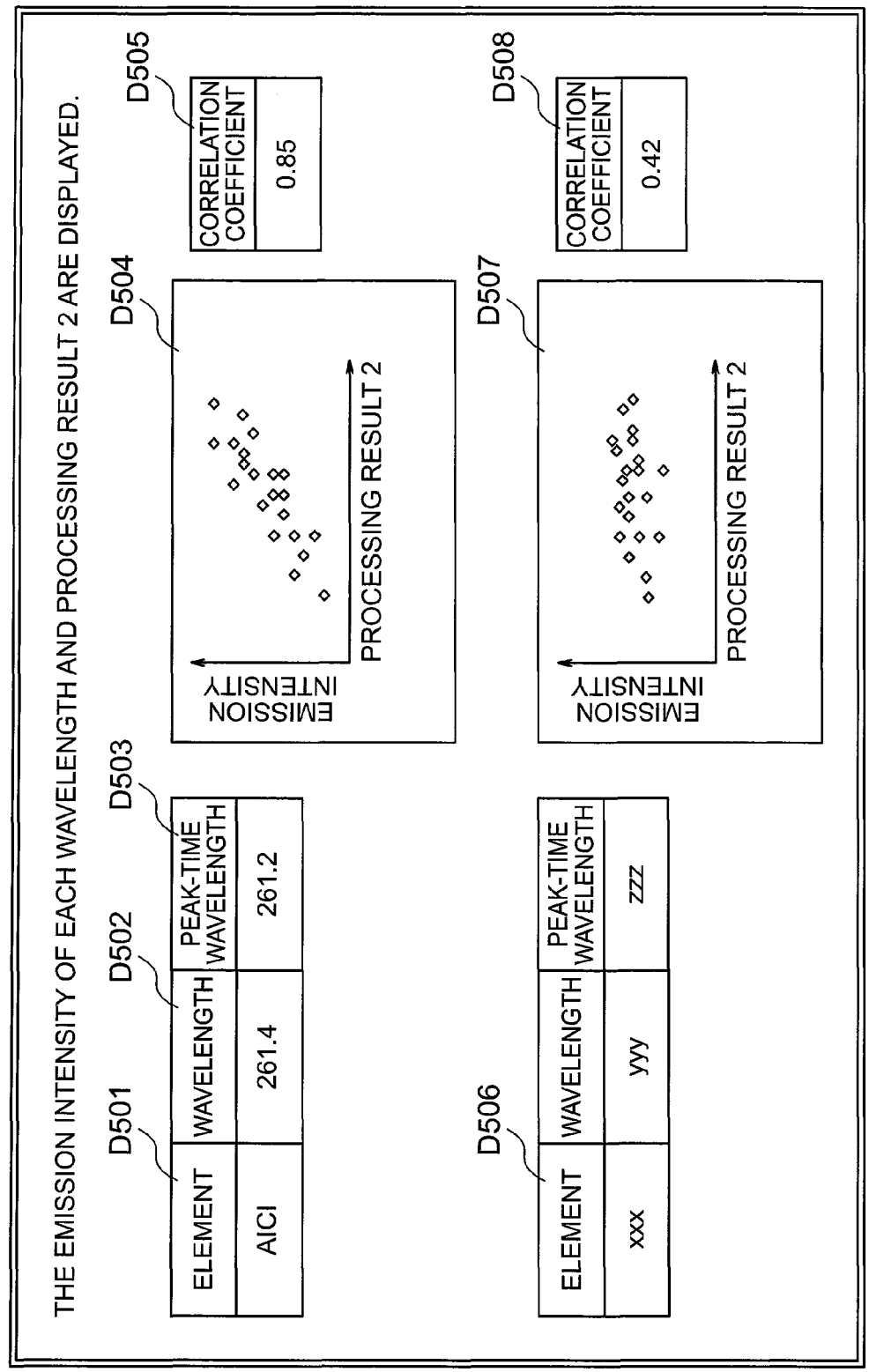

PLASMA PROCESSING APPARATUS AND ANALYZING APPARATUS

INCORPORATION BY REFERENCE

The present application claims priority from Japanese application JP2013-052634 filed on Mar. 15, 2013, the content of which is hereby incorporated by reference into this application.

BACKGROUND OF THE INVENTION

The present invention relates to a semiconductor etching apparatus for processing a semiconductor wafer using plasma and to an analyzing apparatus.

In order to form miniaturized shapes such as those of a semiconductor device on a wafer, material is ionized (is placed in the plasma state) and the etching processing is performed for removing material on the wafer through the operation (reaction at the surface of the wafer) of the ionized material.

Because an ionization event caused by plasma involves a lightning phenomenon, an etching apparatus, which performs processing using plasma, has an optical emission spectroscope (OES) mounted thereon to monitor light emitted by plasma. Data measured by an optical emission spectroscope is hereinafter called OES data.

OES data is composed of a plurality of wavelengths and the values of light emission intensity measured at points in time. Because there are several thousand of wavelengths, the problem is that a wavelength to be analyzed must be selected from such a large number of wavelengths.

As a method for identifying a wavelength to be analyzed, the methods described in Japanese Patent No. 3179997 (corresponding to U.S. Pat. No. 5,546,322) and Japanese Patent No. 4086190 are known. Japanese Patent No. 3179997 describes a method in which a plurality of specified elements (atom, ion, compound, etc.) is made to correspond to each wavelength of an emitted light generated by the plasma processing and this correspondence is displayed to an analyzer. Based on the elements displayed in this correspondence, the analyzer determines a wavelength and finds the correlation between the value of the emitted light at the wavelength and the etching processing result.

Japanese Patent No. 4086190 describes a method in which, for a specified wavelength, an element that is the cause of light emission at the specified wavelength is identified.

To do so, the analyzer first identifies a wavelength, related to the etching processing result, using some method and, after that, uses the disclosed method to find an element related to the etching processing result.

SUMMARY OF THE INVENTION

However, the method described in Japanese Patent No. 3179997 selects and displays all wavelengths corresponding to the plurality of specified elements with the result that many wavelengths are displayed. The problem with this method is that it takes time for the analyzer to select a wavelength to be analyzed.

The method described in Japanese Patent No. 4086190 helps the analyzer with the analysis after the analyzer selects a wavelength but does not provide a method for selecting a wavelength, which is to be analyzed, from many wavelengths. The problem with this method is that it takes time for the analyzer to select a wavelength to be analyzed.

In order to reduce the analysis time, it is an object of the present invention to provide an ability to identify a wavelength, which is used in the analysis of etching processing, from OES data generated by observing light emission during the etching.

To achieve the object described above, according to an aspect of the present invention, the present invention calculates an emission intensity in the vicinity of each of a plurality of wavelengths, at which a specified element should emit light, from information indicating light emission measured by an optical emission spectroscope during etching processing and, if it is determined that the calculated emission intensity information and emission intensity information stored in a storage unit are similar, extracts a wavelength, corresponding to the calculated emission intensity, with the wavelength associated with the element.

The present invention allows a wavelength, which is used in the analysis of etching processing, to be selected from OES data, thereby reducing the time required for the analysis.

Other objects, features and advantages of the invention will become apparent from the following description of the embodiments of the invention taken in conjunction with the accompanying drawings.

BRIEF DESCRIPTION OF THE DRAWINGS

FIG. 5 is a diagram showing an example of a table containing an etching processing result.

FIG. 6 is a diagram showing an example of a table containing the correspondence between elements and wavelengths.

FIG. 7 is a diagram showing an example of a table containing thresholds.

FIG. 8 is a diagram showing an example of a table containing element light-emission states.

FIG. 9 is a diagram showing an example of a table containing recommended wavelengths.

FIG. 16 is a diagram showing a display screen in one embodiment of the present invention.

DETAILED DESCRIPTION OF THE EMBODIMENTS

Figure 1:
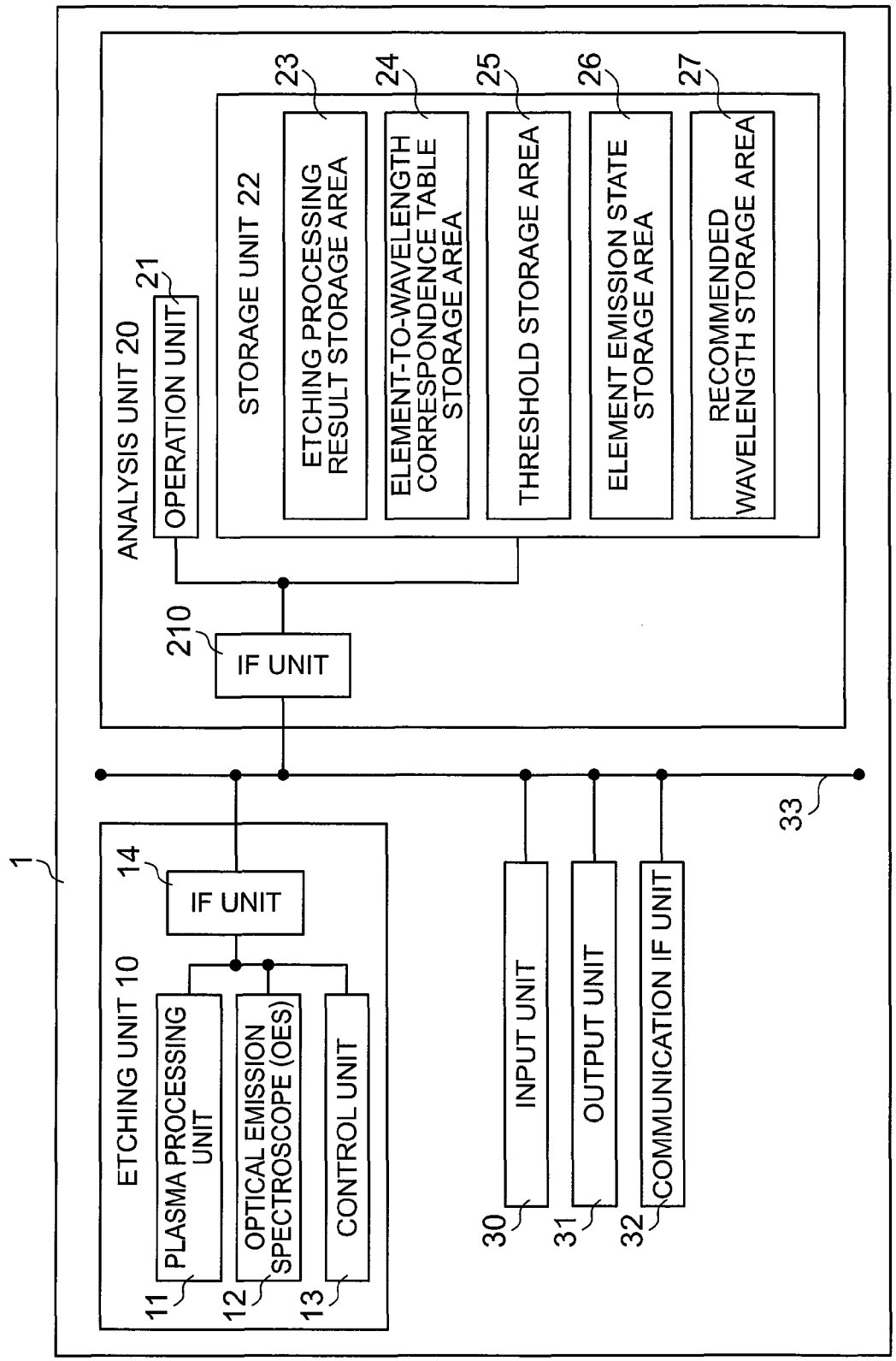
FIG. 1 is a diagram showing a configuration of an etching apparatus in one embodiment of the present invention.

An embodiment of the present invention is described below in detail with reference to the drawings. In all of the drawings for describing the embodiment, the same reference numeral is given to components having the same function and repetitive description will not be given.

[Etching Apparatus]

As shown in the configuration diagram of an etching apparatus in FIG. 1, an etching apparatus 1 of the present invention includes an etching unit 10, an analysis unit 20, an input unit 30, an output unit 31, and a communication interface (IF) unit 32. These units are interconnected via a bus 33.

The etching unit 10 includes a plasma processing unit 11, an optical emission spectroscope (OES) 12, a control unit 13, and an interface (IF) unit 14. The plasma processing unit 11 generates plasma for processing a wafer. The optical emission spectroscope (OES) 12 acquires OES data that is plasma light emission data generated during the etching processing. The OES data is stored in a storage unit 22 of the analysis unit 20 via the IF unit 14. The control unit 13 controls the processing performed by the plasma processing unit 11. The detail of the etching unit 10 will be described later with reference to FIG. 2.

The analysis unit 20 includes an operation unit 21 that performs operation processing for collected OES data; the storage unit 22 that stores OES data, data indicating the predetermined wavelength and emission intensity of light emitted by each of the elements, and the processing result of the operation unit 21; and an IF unit 210. The operation unit 21 acquires emission intensity values from the OES data, calculates the ranks of emission intensities of wavelengths for a plurality of specified wavelengths, and calculates the emission intensity similarity by calculating the number of transpositions performed before the calculated ranks match the predetermined emission intensity ranks and, based on the level of the similarity of emission intensity, identifies a wavelength to be used in the analysis of the etching processing. The detail of the operation processing performed by the operation unit 21 will be described later with reference to FIG. 11.

The input unit 30 is a mouse or a keyboard via which information is received through user operation. The output unit 31 is a display or a printer from which information is output to the user. The communication IF unit 32 is an interface via which the etching apparatus 1 connects to other apparatuses (connectable also to an inspection apparatus for measuring etching processing results) or to a system (connectable also to an existing production management system) via the bus 33 and an external network for sending and receiving information. The bus 33 links the units (10, 20, 30, 31, and 32) of the etching apparatus 1. The IF unit (14, 210) of each unit is an interface for sending and receiving information via the bus 33. The analysis unit 20 may be configured as an independent analysis apparatus that connects to the etching apparatus, which includes an etching unit, via the IF unit.

[Etching Unit]

Figure 2:
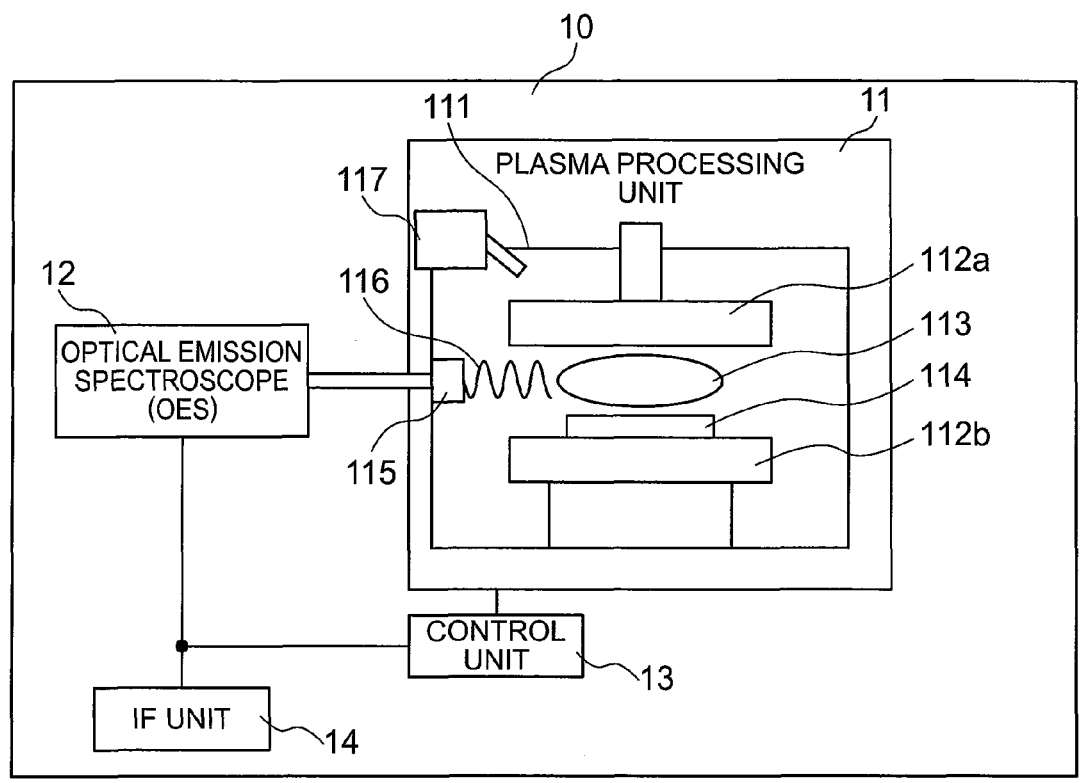
FIG. 2 is a diagram showing a configuration of an etching unit in one embodiment of the present invention.

The etching unit 10 includes the plasma processing unit 11, optical emission spectroscope (OES) 12, control unit 13, and IF unit 14. As shown in FIG. 2, the plasma processing unit 11 includes a chamber 111, electrodes 112a and 112b, a window 115, and a gas supplier 117. In response to an instruction from the control unit 13, the plasma processing unit 11 places a wafer 114 in the chamber 111, supplies etching gas from the gas supplier 117, and applies gas 113, plasmatized by applying a voltage using the electrodes 112a and 112b, to the wafer 114 to process the wafer 114. The gas 113 includes elements, included in the etching gas supplied from the gas supplier 117, and elements generated during the processing of the wafer 114. Light 116 with a wavelength, corresponding to the elements included in the gas, is generated. The generated light is measured by the optical emission spectroscope (OES) 12 through the window 115.

After the etching processing is terminated, the processed wafer 114 is conveyed to other apparatuses (an inspection apparatus or a measurement apparatus) and another wafer 114 is placed in the etching unit 10 for the etching processing. The processed wafer 114 is inspected or measured by other apparatuses (inspection apparatus and measurement apparatus) if it has an intended shape and size as a result of the etching processing.

[OES Data]

Figure 3:
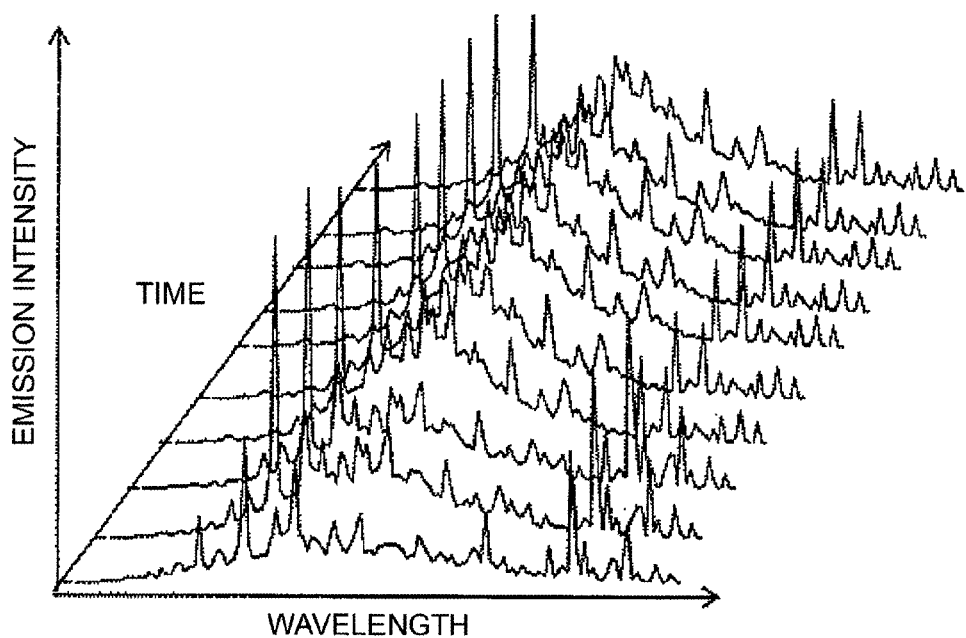
FIG. 3 is a diagram showing an example of OES data.
Figure 4:
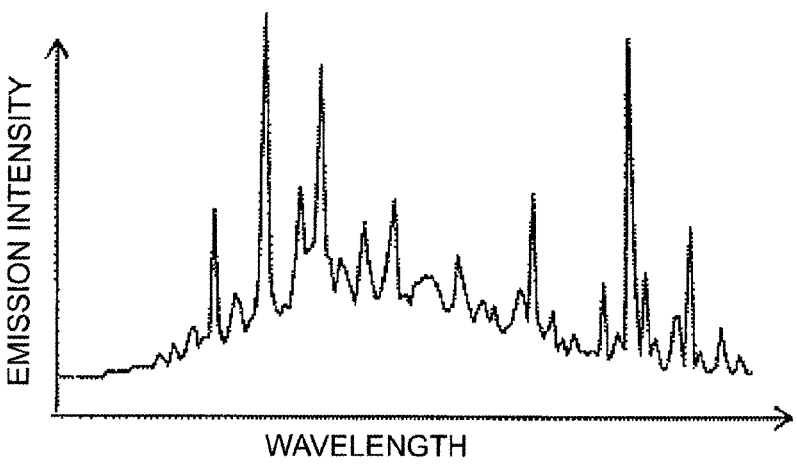
FIG. 4 is a diagram showing an example of OES data at a particular point in time or OES data averaged for a particular time duration.

FIG. 3 is a diagram showing an example of OES data measured by the optical emission spectroscope (OES) 12. The OES data, which has two-dimensional elements (wavelength and time), represents the value of emission intensity measured for each wavelength at each point in time. FIG. 4 is a diagram showing the emission intensity at each wavelength at a particular point in time or the average value of the emission intensities at each wavelength for a particular time width. The values shown in FIG. 4, that is, the emission intensity of each wavelength at a particular point in time or the average value of the emission intensities at each wavelength for particular time duration, are stored in an etching processing result storage area 23 described later.

[Analysis Unit]

As shown in FIG. 1, the analysis unit 20 includes the operation unit 21, storage unit 22, and IF unit 210. The storage unit 22 includes the etching processing result storage area 23, an element-to-wavelength correspondence table storage area 24, a threshold storage area 25, an element emission state storage area 26, and a recommended wavelength storage area 27.

The etching processing result storage area 23 stores information that identifies OES data measured by the optical emission spectroscope (OES) 12 and information that identifies etching processing results.

FIG. 5 is a diagram showing an etching processing result table 23a, an example of the etching processing result storage area 23. This table has fields such as a wafer ID column 23b, a wavelength emission-intensity column 23c, a processing result 1 column 23d, and a processing result 2 column 23e.

The wafer ID column 23b stores information that identifies the wafer 114. The wavelength emission-intensity column 23c stores information that identifies the emission intensities included in the OES data measured at etching processing time of the wafer 114 identified by the wafer ID column 23b. A value identified in this column indicates the emission intensity at each wavelength at a particular point in time. A value may also be the time average value of emission intensities at each wavelength for an arbitrary time duration.

The processing result 1 column 23d stores non-numeric information that indicates whether the etching processing result is good. For example, this column stores the result of determination indicating whether the wafer 114 identified by the wafer ID column 23b is good. This result is generated after the etching processing by an inspection apparatus connected to the etching apparatus 1. For each wafer, the information about the inspection result, such as "fair" or "excellent", is stored in the etching processing result storage area 23 via the communication IF unit 32.

The processing result 2 column 23e stores numeric information indicating whether the etching processing result is good. For example, this column stores the result of measurement of the surface shape of the wafer 114 identified by the wafer ID column 23b. This result is obtained after the etching processing by a measurement apparatus connected to the etching apparatus 1. The size information about the surface shape for each wafer is stored in the etching processing result storage area 23 via the communication IF unit 32.

FIG. 6 is a diagram showing an element-to-wavelength correspondence table 24a, an example of the element-to-wavelength correspondence table storage area 24. This table has the fields such as an element column 24b, a wavelength column 24c, an emission intensity column 24d, and a rank column 24e.

The element column 24b stores information that identifies elements that may be included in the gas 113. The wavelength column 24c stores information that identifies the wavelength of light emitted by the element identified by the element column 24b. The wavelength identified by the wavelength column 24c is the wavelength measured and identified in advance.

The emission intensity column 24d stores information that identifies the intensity of light emitted by the element, identified by the element column 24b, at the wavelength identified by the wavelength column 24c. The emission intensity identified by the emission intensity column 24d is the emission intensity measured and identified in advance. This information, which is referenced to identify an element that emits light during the etching processing, may be used as the information (master data) that should be stored before the etching processing is performed, for example, at a product shipment time.

The rank column 24e stores information that indicates the rank of the value in the emission intensity column 24d in this row among the values in the emission intensity column 24d when multiple rows contain the same element identified by the element column 24b. The information stored in the rank column 24e, which is calculated in the processing flow described later, may also be given in advance.

Note that the elements described above are not always included in the gas 113. Also note that, except for an error such as a measurement error, the wavelength of light emitted by the same element is the same even if the condition of the etching apparatus 1 differs. The absolute value of emission intensity differs according to the condition of the etching apparatus 1, but the relative relation among the emission intensities of the same element remains almost the same. Therefore, the ranks of the values of the emission intensity of the same element do not change much even if the condition of the etching apparatus 1 differs.

FIG. 7 is a diagram showing a threshold table 25a, an example of the threshold storage area 25. This table has a threshold column 25b. The threshold column 25b stores a value used for the determination in the processing that will be described later.

FIG. 8 is a diagram showing an element emission state table 26a, an example of the element emission state storage area 26. This table has the fields such as an element column 26b, a wavelength column 26c, a specified element column 26d, an emission intensity column 26e, and a rank field 26f.

The element column 26b stores information that identifies elements that may be included in the gas 113. The information stored in the element column 26b is the same information as that stored in the element column 24b of the element-to-wavelength correspondence table 24a described above.

The wavelength column 26c stores information that identifies the wavelength of light emitted by the element identified by the element column 26b. The information stored in the wavelength column 26c is the same information as that stored in the wavelength column 24c of the element-to-wavelength correspondence table 24a described above.

The specified element column 26d stores information that identifies an element specified by the analyzer as an analysis target. A plurality of wavelengths is related to one element in this example, and "∘" is stored for all wavelengths of an element specified by the analyzer.

The emission intensity column 26e stores information that identifies the peak value of emission intensity in the vicinity of the wavelengths identified by the wavelength column 26c. If it is determined in the processing described later that there is no peak, "−" is stored to indicate that there is no peak.

The rank field 26f stores information that identifies the rank of the value, stored in the emission intensity column 26e, among the same element. The rank is determined in the descending order of the emission intensity of the wavelengths.

FIG. 9 is a diagram showing a recommended wavelength table 27a, an example of the recommended wavelength storage area 27. This table has the fields such as an element column 27b, a wavelength column 27c, a recommended element column 27d, and a recommended wavelength column 27e.

The element column 27b stores information that identifies elements that may be included in the gas 113. The information stored in the element column 27b is the same information as that stored in the element column 24b of the element-to-wavelength correspondence table 24a described above.

The wavelength column 27c stores information that identifies the wavelength of light emitted by the element identified by the element column 27b. The information stored in the wavelength column 27c is the same information as that stored in the wavelength column 24c of the element-to-wavelength correspondence table 24a described above.

The recommended element column 27d stores information that identifies an element that is identified by the element column 27b and is selected as an analysis target. The recommended wavelength column 27e stores information that identifies a wavelength that is identified by the wavelength column 27c and is selected as an analysis target.

[Analysis Processing of Analysis Unit 20]

Figure 10:
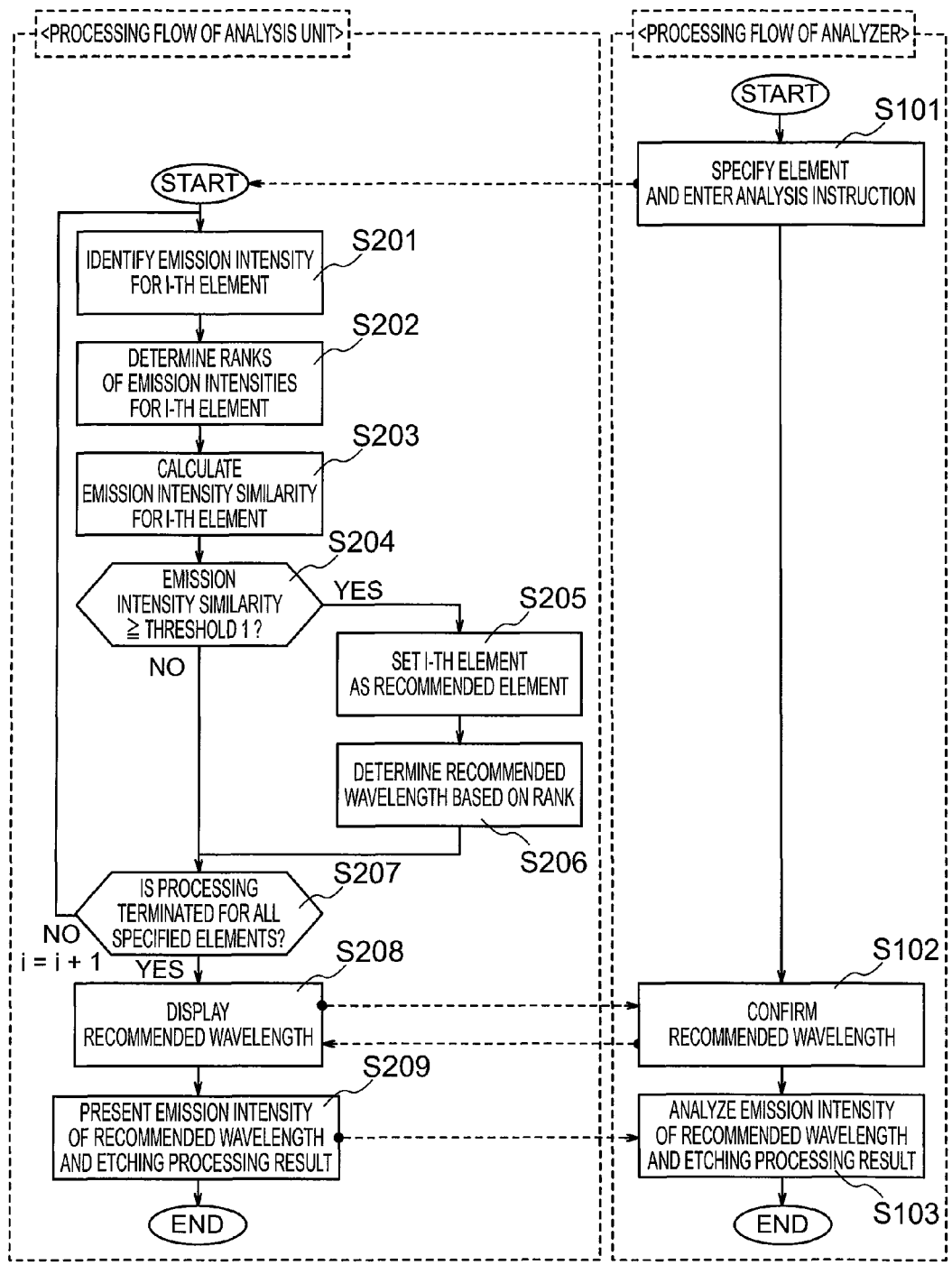
FIG. 10 is a diagram showing the processing flow of an analyzer and an analysis unit in one embodiment of the present invention.

FIG. 10 is a flowchart showing the processing performed by the analyzer and the analysis processing performed primarily by the operation unit 21 of the analysis unit 20. A processing step having a processing step number beginning with S1, such as S101, indicates a processing step performed by the analyzer while a processing step having a processing step number beginning with S2, such as S201, indicates analysis processing performed by the analysis unit 20. The following describes the analysis processing with reference to FIG. 10.

(S101)

Figure 11:
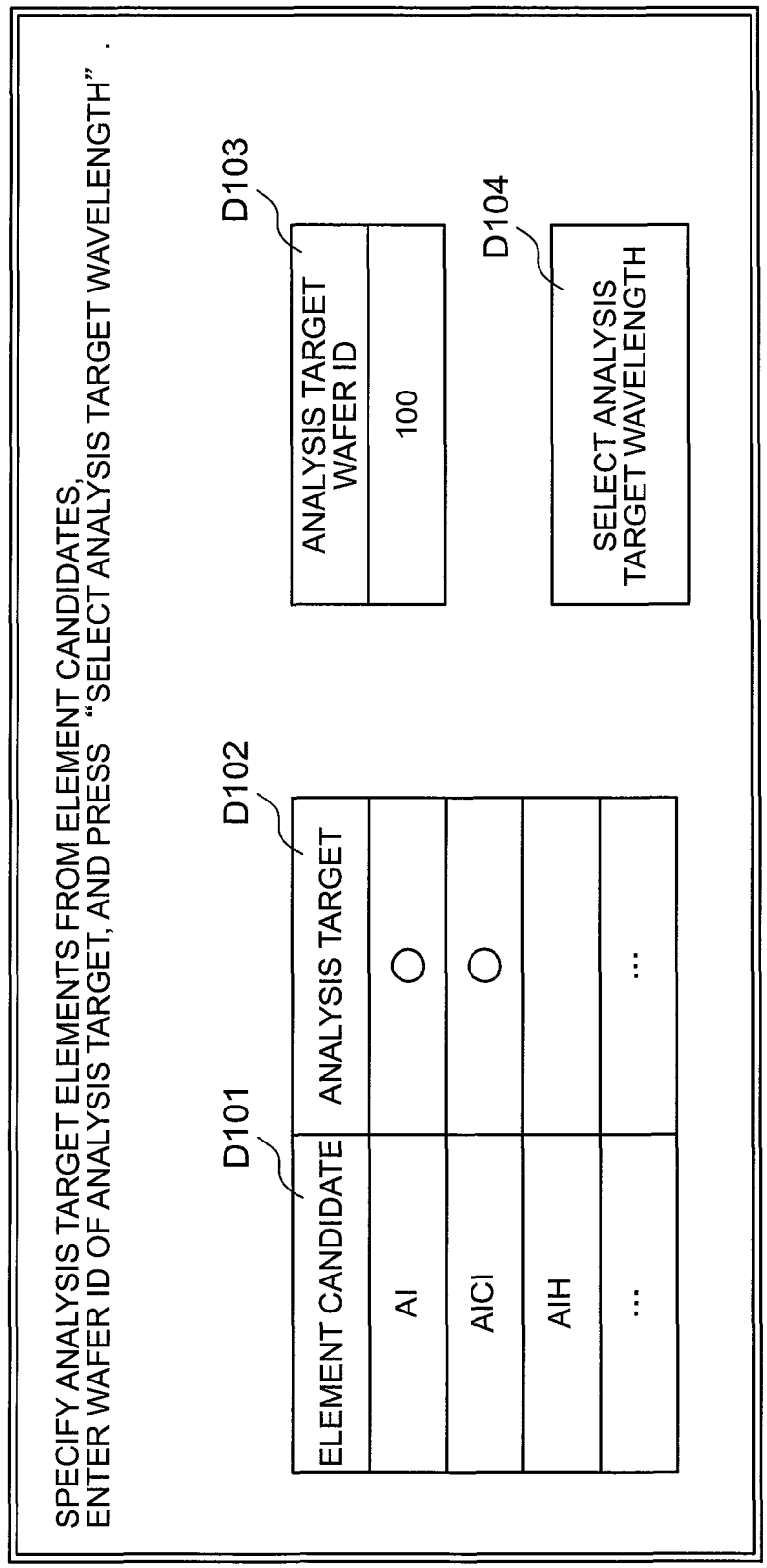
FIG. 11 is a diagram showing a display screen in one embodiment of the present invention.

When analyzing the relation between the light emission data and the etching processing results, the analyzer first selects an element, which the analyzer wants to specify as an analysis target, from the Element candidate column (D101) on the input screen, shown in FIG. 11, and enters "∘" in the Analysis target column (D102) corresponding to the element the analyzer wants to specify. In addition, the analyzer enters the wafer ID of an analysis-target wafer in the Analysis target wafer ID column (D103). After entering the values in those columns, the analyzer clicks the button stating that "Select analysis target wavelength (D104)". When this button is clicked, the analysis unit 20 starts the analysis processing. In the description below, the value entered in the Analysis target wafer ID column (D103) is called a WID.

The elements specified in D102 may be information about an element of the etching gas or information about an element of the semiconductor wafer.

Before the analysis processing is started, the values are already stored in the etching processing result table 23a, element-to-wavelength correspondence table 24a, and threshold information table 25a. The etching processing result table 23a stores the values measured by the optical emission spectroscope (OES) 12 and the values measured by the inspection apparatus or the measurement apparatus. The element-to-wavelength correspondence table 24a stores, in advance, the values collected by past experiments. The threshold information table 25a stores the values determined by the designer. The element column 26b and the wavelength column 26c of the element emission state table 26a and the element column 27b and the wavelength column 27c of the recommended wavelength table 27a store, respectively, the value of the element column 24b and the value of the wavelength column 24c of the element-to-wavelength correspondence table 24a. Although the values are stored in the rank column 24e of the element-to-wavelength correspondence table 24a during the processing S202 that will be described later, the values may also be stored in advance by the designer.

(Processing from S201 to S207)

The operation unit 21 assigns numbers, i=1, 2, . . . , n, to the elements for which "○" is entered in the Analysis target column (D102), sequentially beginning with the top row. In the description below, an element for which "○" is entered and is the i-th entry from the top is called the i-th element.

The operation unit 21 performs the processing in S201 with 1 assigned to i (i=1) and then repeats the processing, S201 to S207, until i reaches n (i=n) (that is, until the processing is performed for all elements specified by the analyzer).

(S201)

In S201, for the i-th element, the operation unit 21 stores the values, required for the calculation, in the specified element column 26d and the emission intensity column 26e of the element emission state table 26a as described below. First, the operation unit 21 checks the values stored in the element column 26b of the element emission state table 26a and, for one or more rows whose value of the element column 26b is equal to the i-th element, stores "○" in the specified element column 26d.

Figure 12A:
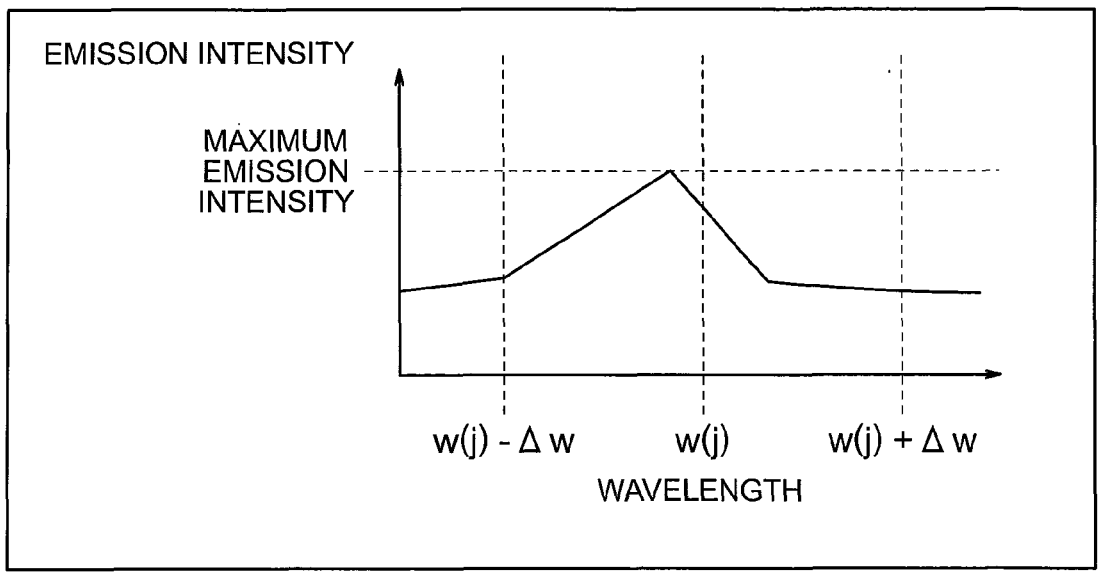
FIGS. 12A and 12B are diagrams showing the processing of the analysis unit in one embodiment of the embodiment of the present invention.
Figure 12B:
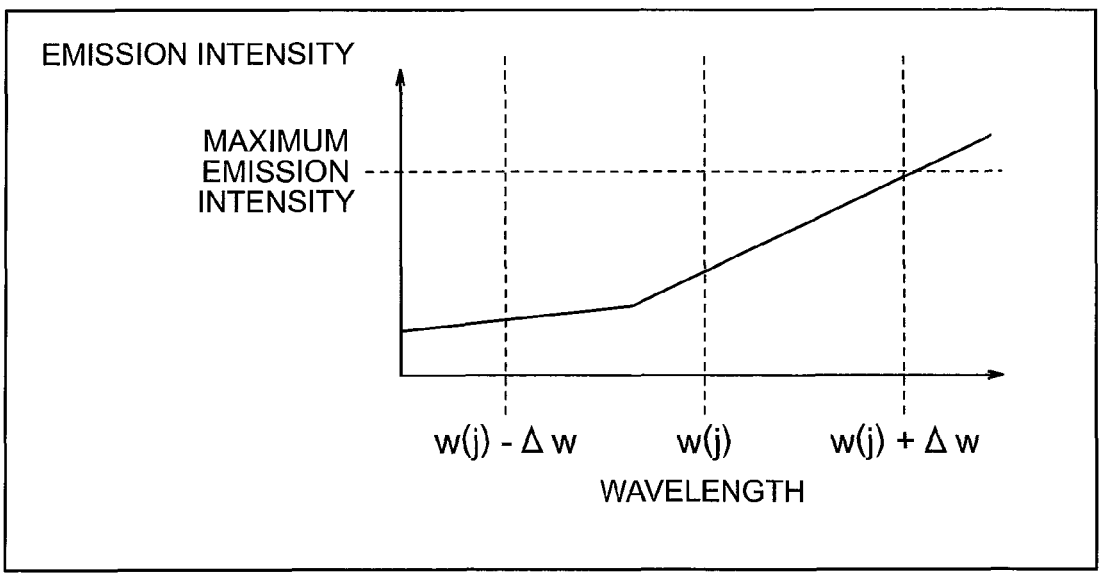

In addition, the operation unit 21 checks the values stored in the element column 26b of the element emission state table 26a and, for one or more rows whose value of the element column 26b is equal to the i-th element, acquires the values stored in the wavelength column 26c, one value for each row. For the same element, w(j) (j=1, 2, . . . , m) is an acquired wavelength value assigned sequentially beginning with the top. The operation unit 21 performs the following processing for each of w(j). The operation unit 21 performs the processing for a column which is included in the etching processing result table 23a and whose value in the wafer ID column 23b is equal to WID. From this column, the operation unit 21 reads the values which are stored in the wavelength emission-intensity column 23c and whose wavelength is in the range from w(j)−Δw to w(j)+Δw (for example, Δw is 0.5) and then calculates the maximum of the values that are read. If the value stored for the wavelength w(j)−Δw or for the wavelength w(j)+Δw is not the maximum value, the operation unit 21 assumes that there is the emission-intensity peak (wavelength whose emission intensity is higher than the emission intensities of the surrounding wavelengths) in the vicinity of the wavelength w(j) as shown in FIG. 12A and stores the emission-intensity value in the emission intensity column 26e in the row corresponding to w(j). When there is a peak in the vicinity of the wavelength w(j), the peak is most likely caused by the light emission of the i-th element. If the value stored for the wavelength w(j)−Δw or for w(j)+Δw is the maximum value, the operation unit 21 stores "−" in the emission intensity column 26e in the row corresponding to w(j), assuming that there is no peak in the vicinity of the wavelength w(j) as shown in FIG. 12B. Note that even when the peak in the vicinity is caused by the light emission of an element, the value of the wavelength of light emitted by the element does not completely match the value of the wavelength at the peak in many cases. The reason is that this error is caused, for example, by a measurement error of the optical emission spectroscope.

(S202)

In S202, the operation unit 21 stores the values, required for the calculation, in the rank column 24e of the element-to-wavelength correspondence table 24a and in the rank field 26f of the element emission state table 26a for the i-th element as described below.

First, the operation unit 21 searches the element-to-wavelength correspondence table 24a for rows (one or more) whose value in the element column 24b is equal to the i-th element. If no value is stored in the rank columns 24e of the identified rows, the operation unit 21 performs the following processing to store values in the rank columns 24e. The operation unit 21 reads the values in the emission intensity column 24d of the rows (that is, in rows for the i-th element) and identifies the ranks sequentially in the descending order of the values that are read. The operation unit 21 identifies the ranks until the number of rank values reaches a predetermined numeric value. This is because data with higher emission intensity is considered to have lower noise and higher accuracy. In the embodiment in FIG. 6, the rank is determined for the highest two values and the columns of data having the third or lower highest emission intensity are left blank. The operation unit 21 stores the identified rank values in the rank columns 24e in the corresponding rows.

Next, the operation unit 21 searches the element emission state table 26a for rows (one or more rows) whose value in the element column 26b is equal to the i-th element and reads the numeric values stored in the emission intensity column 26e of the identified rows. The operation unit 21 identifies the ranks in the descending order of the numeric values that are read (in the rows for the i-th element). The operation unit 21 stores the identified rank values in the corresponding rows of the rank field 26f. In addition, the operation unit 21 stores "−" in a row, in which no numeric value is stored in the emission intensity column 26e, to indicate that no numeric value is stored in the row of the rank field 26f.

(S203)

In S203, the operation unit 21 calculates, for the i-th element, the emission intensity similarity using the values stored in the rank column 24e of the element-to-wavelength correspondence table 24a and the values stored in the rank field 26f of the element emission state table 26a as described below.

First, the operation unit 21 searches the element-to-wavelength correspondence table 24a for rows (one or more) whose value in the element column 24b is equal to the i-th element. After that, the operation unit 21 reads the values stored in the identified rows of the wavelength column 24c and the values stored in the identified rows of the rank column 24e and arranges the values, stored in the wavelength column 24c, in the order indicated by the values stored in the rank column 24e. When the element A1 is processed in the embodiment shown in FIG. 6, the values are arranged in the sequence of "396" and "394.4". The sequence identified in this processing is called the sequence I.

Next, the operation unit 21 searches the element emission state table 26a for rows (one or more) whose value in the element column 26b is equal to the i-th element. After that, the operation unit 21 reads the values stored in the identified rows of the wavelength column 26c and the values stored in the identified rows of the rank field 26f and arranges the values, stored in the wavelength column 26c, in the order indicated by the values stored in the rank field 26f. In this processing, the columns in which "−" is stored are excluded. When the element A1 is processed in the embodiment in shown FIG. 8, the sequence is arranged in the order of "308.2", "394.4", and "396". The sequence identified here is called the sequence A. In addition, the operation unit 21 calculates the emission intensity similarity using the sequence I and the sequence A.

First, the operation unit 21 sets the emission intensity similarity to 0 when a value included in the sequence I is not included in the sequence A. In other cases, the operation unit 21 transposes the neighboring values in the sequence A, one pair of values at a time, and calculates the number of times the transposition is performed until the transposed values in the sequence A match the values in the sequence I beginning at the start of the sequences. In this case, a value included in the sequence A but not included in the sequence I may be in any position. When the element A1 is processed using the embodiment sin FIG. 6 and FIG. 8, the calculated number of transpositions is three as follows.

Initial sequence A: "308.2", "394.4", "396"
First transposition: "308.2", "396", "394.4" ("396" and "394.4" are transposed)
Second transposition: "396", "308.2", "394.4" ("396" and "308.2" are transposed)
Third transposition: "396", "394.4", "308.2" ("394.4" and "308.2" are transposed)

The operation unit 21 divides the number of transpositions by the number of elements of the sequence A and then subtracts 1 from the result to calculate the emission intensity similarity of the i-th element. When the element A1 is processed in the embodiments shown in FIG. 6 and FIG. 8, the emission intensity similarity is calculated as 1−3/3=0.

A low emission-intensity similarity indicates that light emission distribution of the i-th element collected by experiments is different from the light emission distribution of the i-th element obtained by the etching processing. In the case of etching processing, the light emission distribution of the same element remains similar even when the condition of the etching apparatus 1 differs. Therefore, a low similarity indicates that the emission-intensity peak corresponding to the wavelength of the i-th element is caused, not by the light emission of the i-th element, but by another factor (noise or light emission of some other element). If the information about light emission, caused by another factor, is provided as the information indicating that the light emission is caused by the i-th element, the analyzer will make an error in determining the cause of light emission and in taking measures against this condition. To avoid such a situation, the processing in S204 and S206 is performed as described below to allow the analyzer to determine the wavelength of the analysis target based on emission intensity similarity.

(S204)

In S204, the operation unit 21 determines the processing to be executed next based on the emission intensity similarity as described below. If the emission intensity similarity is equal to or higher than the value stored in the threshold 1 column 25b of the threshold table 25a, the operation unit 21 performs the processing in S205 next. If the emission intensity similarity is lower than the value stored in the threshold 1 column 25b of the threshold table 25a, the operation unit 21 performs the processing in S207 next. Note that the threshold column may store multiple values other than threshold 1, such as threshold 2, for switching the threshold from one value to another.

(S205)

In S205, the operation unit 21 stores values in the recommended element column 27d of the recommended wavelength table 27a as described below. The operation unit 21 searches the recommended wavelength table 27a for rows (one or more) whose value of the element column 27b is equal to the i-th element and stores "○" in the identified rows of the recommended element column 27d to indicate that the element is a recommended element.

(S206)

In S206, the operation unit 21 stores values in the recommended wavelength column 27e of the recommended wavelength table 27a as described below. The operation unit 21 searches the recommended wavelength table 27a for rows (one or more) whose value of the element column 27b is equal to the i-th element. For those rows, the operation unit 21 identifies rows for which rank values are specified in advance in the rank column (highest rank in this embodiment) and identifies the wavelengths in the wavelength column 27c corresponding to the rank values. The identified wavelengths are called a high-level wavelength.

In addition, the operation unit 21 searches the recommended wavelength table 27a for rows (one or more) whose value of the element column 27b is equal to the i-th element and whose value of the wavelength column 27c is equal to the high-level wavelength described above. After that, the operation unit 21 stores "○" in the recommended wavelength column 27e of the row to indicate that wavelength in this row is the recommended wavelength.

(S207)

After the processing is performed for all elements specified in D102, the operation unit 21 performs the processing in S208 that follows. In other cases, the operation unit 21 increments i by 1 (i=i+1), returns control to the processing in S201, and performs processing, such as the emission intensity similarity calculation, for the element that is specified next.

(S208)

After the processing is performed for all specified elements, the operation unit 21 displays the recommended wavelength. The operation unit 21 displays the display screen, shown in FIG. 13, on the output unit 31 or on an external output device via the communication IF unit 32.

In D201, the value is displayed that is in the element column 27b of the recommended wavelength table 27a and is in a row whose recommended wavelength column 27e stores "○". In D202, the value is displayed that is in the wavelength columns 27c of the recommended wavelength table 27a and is in a row whose recommended wavelength column 27e stores "○". In D203, the values of a column, which is one of the wavelength emission-intensity columns 23c of the etching processing result table 23a and whose value of the wafer ID column 23b is equal to WID, are displayed. These values are displayed as a graph in which the horizontal axis indicates the wavelength and the vertical axis indicates the emission intensity. As shown in this embodiment, a part of the stored values may be enlarged when displayed.

In D204, the element and the wavelength, displayed in D201 and D202 respectively, are displayed on the graph in D203. The peak in the vicinity (in the range from displayed wavelength−Δw to displayed wavelength+Δw) of the wavelength displayed in D202 is identified and, near the wavelength of the identified peak, the value of the peak-time wavelength, the name of the element displayed in D201, and the value of the wavelength displayed in D202 are displayed.

D205 is a button that is pressed by the analyzer to analyze a change in the emission intensity during the etching processing that is executed multiple times. D206 is a button that is pressed by the analyzer to analyze the relation between the emission intensity at the displayed wavelength and the value stored in the processing result 1 column 23d of the etching processing result table 23a. D207 is a button that is pressed by the analyzer to analyze the relation between the emission intensity at the displayed wavelength and the value stored in the processing result 2 column 23e of the etching processing result table 23a.

(S102)

Figure 13:
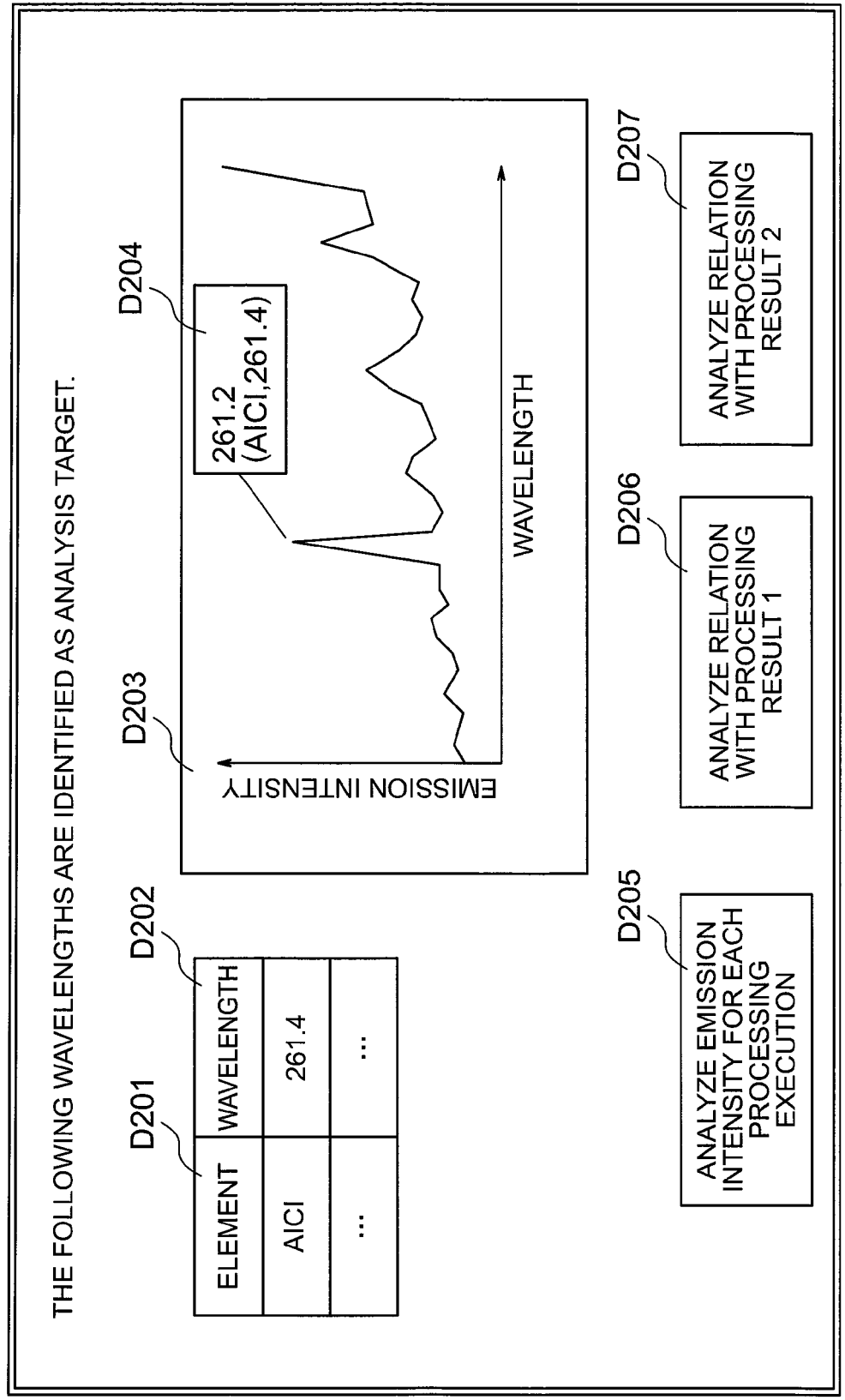
FIG. 13 is a diagram showing a display screen in one embodiment of the present invention.

When the operation unit 21 displays the screen shown in FIG. 13, the analyzer checks the displayed wavelength and determines processing to be performed. The analyzer presses the button shown in D205 to analyze a change in the emission intensity during the etching processing that is executed multiple times (one for each wafer).

The analyzer presses the button shown in D206 to analyze the relation between the non-numeric information, one type of information identifying whether the etching processing result is good, and the emission intensities at the displayed wavelengths. The analyzer presses the button shown in D207 to analyze the relation between the numeric information, one type of information identifying whether the etching processing result is good, and the emission intensities at the displayed wavelengths. When the button shown in D205, D206, or D207 is pressed, the operation unit 21 performs the processing in S209.

(S209)

Figure 14:
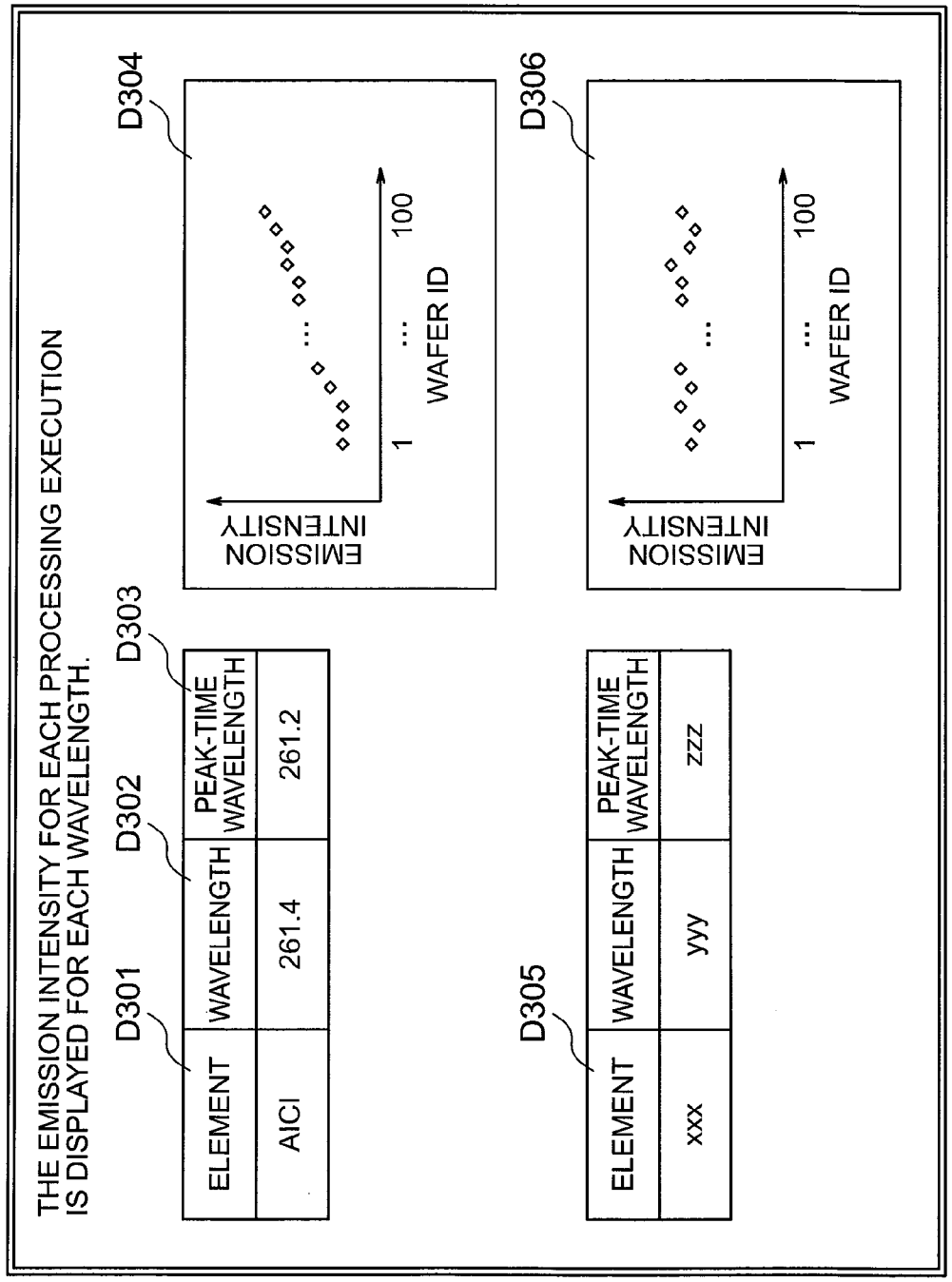
FIG. 14 is a diagram showing a display screen in one embodiment of the present invention.

When the button shown in D205 is pressed, the operation unit 21 displays the screen, shown in FIG. 14, on the output unit 31 or on an external output device via the communication IF unit 32. When the button shown in D206 is pressed, the operation unit 21 displays the screen, shown in FIG. 15, on the output unit 31 or on an external output device via the communication IF unit 32. When the button shown in D207 is pressed, the operation unit 21 displays the screen, shown in FIG. 16, on the output unit 31 or on an external output device via the communication IF unit 32.

First, FIG. 14 is described. In D301, the information indicating the element name, which is included in the information displayed in D204 in FIG. 13, is displayed. In D302, the information indicating the wavelength of light emitted by the element, which is included in the information displayed in D204 in FIG. 13, is displayed. In D303, the information indicating the peak-time wavelength, which is included in the information displayed in D204 in FIG. 13, is displayed.

In D304, the values stored in the wavelength emission-intensity column 23c and the values stored in the wafer ID column 23b in the etching processing result table 23a are displayed. The horizontal axis of D304 indicates the values stored in the wafer ID column 23b, and the vertical axis of D304 indicates the values stored in the wavelength emission-intensity column 23c.

The operation unit 21 identifies a row which is included in the wavelength emission-intensity column 23c and whose wavelength is nearest to the wavelength (peak-time wavelength) displayed in D303 (the row identified here may be a row whose wavelength is nearest to the wavelength (wavelength of element) displayed in D302). For each column of the etching processing result table 23a, the operation unit 21 reads the value of the wavelength emission-intensity column 23c in the identified row and the value of the wafer ID column 23b and plots the value of each column in the graph in D304. In the graph in this example, the values are plotted in such a way that the values stored in the row of the wavelength emission-intensity column 23c correspond to the vertical axis of the graph in D304 and that the values stored in the wafer ID column 23b correspond to the horizontal axis of the graph in D304.

By viewing the screen displayed in D304, the analyzer can easily understand which element's emission intensity follows an increase in the number of times the etching processing is executed. The example shown in FIG. 14 indicates that the emission intensity of AlCl increases as the wafer ID becomes large, that is, as the number of times the etching processing is executed is increased. On the other hand, the emission intensity does not follow an increase in the wafer ID in the distribution (D306) of another element shown in D305. In such a case, the analyzer can determine that there is a possibility that AlCl is related more closely to the number of etching processing executions than other elements are.

Figure 15:
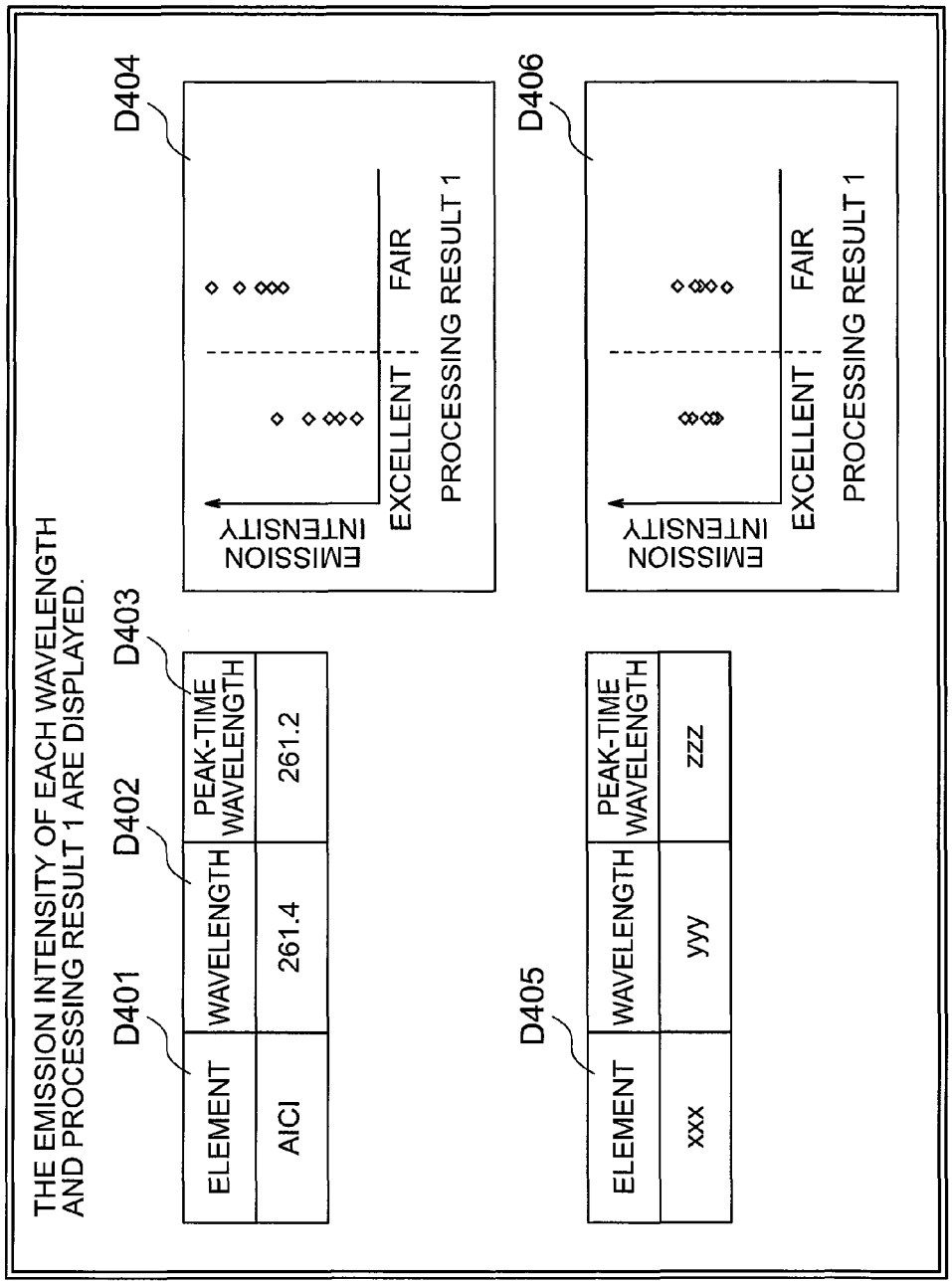
FIG. 15 is a diagram showing a display screen in one embodiment of the present invention.

Next, FIG. 15 is described. In D401, the information indicating the element name, which is included in the information displayed in D204 in FIG. 13, is displayed. In D402, the information indicating the wavelength of light emitted by the element, which is included in the information displayed in D204 in FIG. 13, is displayed. In D403, the information indicating the peak-time wavelength, which is included in the information displayed in D204 in FIG. 13, is displayed.

In D404, the values stored in the wavelength emission-intensity column 23c, and the values stored in the processing result 1 column 23d, of the etching processing result table 23a are displayed. The horizontal axis of D404 indicates the values stored in the processing result 1 column 23d, and the vertical axis of D404 indicates the values stored in the wavelength emission-intensity column 23c.

The operation unit 21 identifies a row which is included in the wavelength emission-intensity column 23c and whose wavelength is nearest to the wavelength (peak-time wavelength) displayed in D403 (the row identified here may be a row whose wavelength is nearest to the wavelength (wavelength of element) displayed in D402). For each column of the etching processing result table 23a, the operation unit 21 reads the value of the wavelength emission-intensity column 23c in the identified row and the value stored in the processing result 1 column 23d and plots the value of each column in the graph in D404. In the graph in this example, the values are plotted in such a way that the values stored in the row of the wavelength emission-intensity column 23c correspond to the vertical axis of the graph in D404 and that the values stored in the processing result 1 column 23d correspond to the horizontal axis of the graph in D404.

By viewing the screen displayed in D404, the analyzer can easily understand which element's emission intensity is related to whether the etching processing result is good. The example shown in FIG. 15 indicates that, when the processing results are different, the difference in the emission intensity of AlCl is larger than the difference in the distribution (D406) of the emission intensities of another element shown in D405. That is, in the case of AlCl, the difference between the emission intensity distribution for "excellent" processing results and the emission intensity distribution for "Fair" processing results is large. In such a case, the analyzer can determine that there is a possibility that AlCl is related more closely to whether the etching processing result is good than other elements are.

Furthermore, FIG. 16 is described. In D501, the information indicating the element name, which is included in the information displayed in D204 in FIG. 13, is displayed. In D502, the information indicating the wavelength of light emitted by the element, which is included in the information displayed in D204 in FIG. 13, is displayed. In D503, the information indicating the peak-time wavelength, which is included in the information displayed in D204 in FIG. 13, is displayed.

In D504, the values stored in the wavelength emission-intensity column 23c, and the values stored in the processing result 2 column 23e, of the etching processing result table 23a are displayed. The horizontal axis of D504 indicates the values stored in the processing result 2 column 23e, and the vertical axis of D504 indicates the values stored in the wavelength emission-intensity column 23c.

The operation unit 21 identifies a row which is included in the wavelength emission-intensity column 23c and whose wavelength is nearest to the wavelength (peak-time wavelength) displayed in D503 (the row identified here may be a row whose wavelength is nearest to the wavelength (wavelength of element) displayed in D502). For each column of the etching processing result table 23a, the operation unit 21 reads the value stored in the identified row of the wavelength emission-intensity column 23c and the value stored in the processing result 2 column 23e and plots the values of each column in the graph in D504. In the graph in this example, the values are plotted in such a way that the values stored in the row of the wavelength emission-intensity column 23c correspond to the vertical axis of the graph in D504 and that the values stored in the processing result 2 column 23e correspond to the horizontal axis of the graph in D504.

In D505, the coefficient of correlation between the values stored in the wavelength emission-intensity column 23c and the values stored in the processing result 2 column 23e of the etching processing result table 23a is displayed as the statistical information.

By viewing the screen displayed in D504, the analyzer can easily understand which element's emission-light wavelength is related to the processing shape (for example, size) obtained as the result of the etching processing. The example shown in FIG. 16 indicates that, as compared with the distribution (D507) and the coefficient of correlation (D508) of another element shown in D506, the coefficient of correlation of the light emission of AlCl with the measurement result of the processing shape, stored in the processing result 2 column 23e, is higher. In such a case, the analyzer can determine that there is a possibility that AlCl is related more closely to the processing shape obtained by the etching processing than other elements are.

As described above, the etching apparatus 1 (analysis unit 20) in this embodiment receives the data measured by the optical emission spectroscope (OES) and the information about the wavelengths and the emission intensities of light emitted by the elements to identify a wavelength that is used in the analysis of the etching processing, thus making the analysis easy.

Although the present invention has been described in detail with reference to a preferred embodiment thereof, it will be understood the present invention is not limited to the embodiment described above but that various changes may be made without departing from the spirit of the present invention.

The invention claimed is:

1. A plasma processing apparatus comprising:
a processing chamber configured for plasma etching processing for a wafer;
an optical emission spectroscope that measures light emission of plasma during the plasma etching processing; and
an analysis unit that includes a storage unit and an operation unit, the storage unit storing, in advance, information about emission intensities at a plurality of wavelengths of light emitted by a predetermined element, wherein:
the operation unit calculates an emission intensity in a vicinity of each of a plurality of wavelengths to be emitted by a specified element, based on information indicating light emission measured by the optical emission spectroscope during the plasma etching processing,
the operation unit determines an order of wavelengths in descending order of calculated respective emission intensity levels,
the operation unit obtains a difference between the order determined by the operation unit and the order of wavelengths in descending order of the respective emission intensity levels stored in advance in the storage unit, and
based at least in part on the difference being smaller than a predetermined value, the operation unit extracts a wavelength, corresponding to the calculated emission intensity, with the wavelength associated with the element.

2. The plasma processing apparatus according to claim 1, wherein
the operation unit associates the calculated emission intensities with information indicating an inspection result or a measured shape size of the wafer, for which the plasma etching processing is performed, and outputs the associated information.

3. The plasma processing apparatus according to claim 2, wherein
the operation unit performs statistical processing for information indicating the inspection result or the measured shape size of a plurality of wafers.

4. The plasma processing apparatus according to claim 1, wherein
the operation unit outputs the extracted wavelength and the corresponding element in a graph indicating the light emission measured by the optical emission spectroscope.

5. The plasma processing apparatus according to claim 1, wherein
the operation unit outputs the wavelength corresponding to the calculated emission intensity and the element in association with information about emission intensities measured according to a number of plasma etching processing executions.

6. A plasma processing apparatus comprising:
a processing chamber configured for plasma etching processing of a wafer;
an optical emission spectroscope that measures light emission of plasma during the plasma etching processing; and
an analysis unit that includes a storage unit and an operation unit, the storage unit storing, in advance, information about emission intensities at a plurality of wavelengths of light emitted by a predetermined element and an order of the wavelengths in descending order of the respective emission intensity levels, wherein:
the operation unit calculates an emission intensity in a vicinity of each of a plurality of wavelengths to be emitted by a specified element based on information indicating light emission measured by the optical emission spectroscope during the plasma etching processing,
the operation unit determines an order of wavelengths in descending order of the respective calculated emission intensity levels,
the operation unit obtains a difference between the order determined by the operation unit and the order stored in advance in the storage unit, and
based at least in part on the difference being smaller than a predetermined value, the operation unit extracts a wavelength, corresponding to the calculated emission intensity, with the wavelength associated with the element.

7. The plasma processing apparatus according to claim 6, wherein
the operation unit associates the calculated emission intensities with information indicating an inspection result or a measured shape size of the wafer for which the plasma etching processing is performed, and outputs the associated information.

8. The plasma processing apparatus according to claim 6, wherein
the operation unit outputs the extracted wavelength and the corresponding element in a graph indicating the light emission measured by the optical emission spectroscope.

9. The plasma processing apparatus according to claim 6, wherein
the operation unit outputs the wavelength corresponding to the calculated emission intensity and the element in association with information about emission intensities measured according to a number of plasma etching processing executions.

* * * * *